US012702845B2

(12) United States Patent
Vedoy et al.

(10) Patent No.: US 12,702,845 B2
(45) Date of Patent: Aug. 11, 2026

(54) IMPLANTABLE MEDICAL DEVICE WITH MOTION DAMPING LAYER

(71) Applicant: Cardiac Pacemakers, Inc., St. Paul, MN (US)

(72) Inventors: Arild Vedoy, Forest Lake, MN (US); Benjamin J. Haasl, Forest Lake, MN (US); Katherine Provo, Plymouth, MN (US); Shane McGrath, Thurles (IE)

(73) Assignee: Cardiac Pacemakers, Inc.

( * ) Notice: Subject to any disclaimer, the term of this patent is extended or adjusted under 35 U.S.C. 154(b) by 268 days.

(21) Appl. No.: 18/432,570

(22) Filed: Feb. 5, 2024

(65) Prior Publication Data

US 2024/0261581 A1 Aug. 8, 2024

Related U.S. Application Data

(60) Provisional application No. 63/443,570, filed on Feb. 6, 2023.

(51) Int. Cl.

| | |
|---|---|
| ***A61N 1/375*** | (2006.01) |
| ***A61N 1/02*** | (2006.01) |
| ***A61N 1/08*** | (2006.01) |

(52) U.S. Cl.

CPC .......... *A61N 1/3758* (2013.01); *A61N 1/025* (2013.01); *A61N 1/08* (2013.01)

(58) Field of Classification Search

None

See application file for complete search history.

(56) References Cited

U.S. PATENT DOCUMENTS

| | | |
|---|---|---|
| 4,014,346 A | 3/1977 | Brownlee et al. |
| 4,254,775 A | 3/1981 | Langer |
| 4,314,562 A | 2/1982 | Ware |
| 5,876,424 A | 3/1999 | O'Phelan et al. |
| 5,999,398 A | 12/1999 | Makl et al. |
| 6,031,710 A | 2/2000 | Wolf et al. |
| 6,428,612 B1 | 8/2002 | McPhilmy et al. |
| 6,603,654 B2 | 8/2003 | Rorvick et al. |
| 6,881,516 B2 | 4/2005 | Aamodt et al. |
| 7,194,309 B2 | 3/2007 | Ostroff et al. |

(Continued)

FOREIGN PATENT DOCUMENTS

| | | |
|---|---|---|
| EP | 2934670 B1 | 1/2018 |
| WO | 2012036944 A1 | 3/2012 |

OTHER PUBLICATIONS

Henkel, Presentation, Macromelt Molding, 35 pages, https://www.ellsworth.com/globalassets/literature-library/manufacturer/henkel-loctite/henkel-presentation-technolmelt-formerly-branded-as-macromelt-molding.pdf Accessed Mar. 2, 2020.

(Continued)

*Primary Examiner* — Carl H Layno
*Assistant Examiner* — Bryan McAllister Lee
(74) *Attorney, Agent, or Firm* — Seager, Tufte & Wickhem LLP

(57) ABSTRACT

Implantable medical devices are constructed with a dampening layer to limit motion of components inside a housing of the implantable medical devices. The dampening layer may have features to provide thermal isolation for certain components. The dampening layer may have features to allow mechanical vibration of selected components. The dampening layer may have features to ensure an air space exists to enable a residual gas analysis test.

20 Claims, 7 Drawing Sheets

(56) References Cited

U.S. PATENT DOCUMENTS 7,263,401 B2 8/2007 Scott et al.
7,485,277 B1 2/2009 Shepodd et al.
7,769,457 B2 8/2010 Fonte
7,968,226 B2 6/2011 Aamodt et al.
8,065,006 B2 11/2011 Rorvick et al.
8,065,007 B2 11/2011 Ries et al.
8,463,393 B2 6/2013 Strother et al.
8,774,921 B2 7/2014 Fonte
9,105,899 B2 8/2015 Pakula et al.
9,713,725 B2 7/2017 Bobgan et al.
10,040,021 B2 8/2018 Ries et al.
10,226,055 B2 3/2019 Rothfuss et al.
10,434,316 B2 10/2019 Kelley et al.
10,894,164 B2 1/2021 Strommer et al.
11,247,059 B2 2/2022 Keller et al.
2003/0204216 A1 10/2003 Ries et al.
2005/0245971 A1 11/2005 Brockway et al.
2008/0221629 A1* 9/2008 Morgan .............. H01M 10/052 29/2
2009/0034769 A1 2/2009 Darley et al.
2010/0305654 A1 12/2010 Fonte
2012/0069536 A1 3/2012 Sporon-Fiedler et al.
2013/0235550 A1 9/2013 Stevenson et al.
2015/0196867 A1 7/2015 Ries et al.
2015/0321013 A1 11/2015 Smith et al.
2016/0066803 A1* 3/2016 Hu ....................... A61B 5/0031 600/561
2016/0151635 A1 6/2016 Frysz et al.
2016/0287865 A1 10/2016 Bobgan et al.
2018/0207427 A1 7/2018 Webb et al.
2019/0168005 A1 6/2019 Li et al.
2019/0321628 A1 10/2019 Stevenson et al.
2020/0054881 A1 2/2020 Frustaci et al.
2020/0121417 A1 4/2020 Prescott et al.
2020/0246625 A1 8/2020 Stevenson et al.
2020/0276440 A1 9/2020 Stevenson et al.
2021/0121705 A1 4/2021 Ries et al.
2022/0047876 A1 2/2022 Becklund et al.
2022/0249852 A1 8/2022 Peterson
2022/0288401 A1 9/2022 Landherr et al.
2023/0256244 A1* 8/2023 John ........................ A61N 1/40 607/118

OTHER PUBLICATIONS

International Search Report and Written Opinion dated Nov. 19, 2021 for International Application No. PCT/US2021/045724.

* cited by examiner

IMPLANTABLE MEDICAL DEVICE WITH MOTION DAMPING LAYER

CROSS REFERENCE TO RELATED APPLICATIONS

The present application claims the benefit of and priority to U.S. Prov. Pat. App. No. 63/443,570, filed Feb. 6, 2023, titled IMPLANTABLE MEDICAL DEVICE WITH MOTION DAMPING LAYER, the disclosure of which is incorporated herein by reference.

BACKGROUND

Implantable medical devices are commonly used today to monitor physiological or other parameters of a patient and/or deliver therapy to a patient. For example, various medical devices (e.g., neural stimulators, pacemakers, defibrillators, cardiac monitors, drug pumps etc.) can be implanted in a patient's body to monitor and/or treat heart and/or nervous system related conditions. Some such devices may monitor and, in some cases, provide electrical therapy (e.g. pacing, defibrillation, neuromodulation, etc.) or other therapy (drug or insulin pumps) to the body. Relative motion between the electrical circuitry and other components within the device may lead to interconnect problems and/or other failures. In some cases, there may be a desire to reduce relative motion within the implantable medical device to increase device reliability. While reducing such relative motion, various particular requirements of the implantable medical device must also be addressed, including inspection and thermal management needs. New and alternative designs are desired.

Overview

The present inventors have recognized, among other things, that a problem to be solved is the need for new and/or alternative designs for an implantable medical device are desired that address inspection and thermal management needs, while reducing internal component motion.

A first illustrative and non-limiting example takes the form of an implantable medical device (IMD) comprising: operational circuitry for performing one or more IMD functions; a battery coupled to the operational circuitry to provide power for the one or more IMD functions, the battery including a header region containing electrical connections to a feedthrough pin, the feedthrough pin used for electrical connection to the operational circuitry; a dampening layer molded over portions of the operational circuitry and at least a first portion of the battery, wherein the dampening layer comprises a first void positioned over the header region of the battery to provide thermal isolation to the header region of the battery.

Additionally or alternatively, the dampening layer has a first thickness over the first portion of the battery, and a second thickness over the header region of the battery, wherein the second thickness is less than the first thickness due to the void. Additionally or alternatively, the dampening layer is omitted entirely over at least a part of the header region of the battery. Additionally or alternatively, the first void of the dampening layer is filled with a thermally isolating tape applied over the header region of the battery. Additionally or alternatively, the first void of the dampening layer is filled with a preform device that is applied over the header region of the battery. Additionally or alternatively, the dampening layer comprises a second void positioned for use in a residual gas analysis test. Additionally or alternatively, the operational circuitry further comprises a speaker, and the dampening layer comprises a third void positioned over the speaker, or the dampening layer comprises an indentation for receiving the speaker without encapsulating the speaker. Additionally or alternatively, the IMD may include an enclosure box in the housing, wherein the operational circuitry further comprises a motion sensor, and the enclosure box surrounds the motion sensor and separates the dampening layer from the motion sensor. Additionally or alternatively, the dampening layer is formed in two parts. Additionally or alternatively, the dampening layer comprises a waffled portion defined by ridges and gaps therebetween, the waffled portion having a reduced thermal conductivity than at least one other portion of the dampening layer.

Another illustrative, non-limiting example takes the form of an implantable medical device (IMD) comprising: operational circuitry for performing one or more IMD functions; a battery coupled to the operational circuitry to provide power for the one or more IMD functions, the battery including a header region containing electrical connections to a feedthrough pin, the feedthrough pin used for electrical connection to the operational circuitry; a dampening layer molded over portions of the operational circuitry and at least a first portion of the battery, wherein the dampening layer comprises a first void positioned for use in a residual gas analysis test.

Additionally or alternatively, the IMD further includes a molded thermal isolation layer on the header region of the battery, thermally separating the dampening layer from the header region of the battery. Additionally or alternatively, the dampening layer has a first thickness over the first portion of the battery, and a second thickness in a selected area over at least part of the headspace region of the battery, the selected area of the dampening layer having an air gap thereover, and the second thickness is less than the first thickness. Additionally or alternatively, the dampening layer has a second void defining an air gap over a header region of the battery. Additionally or alternatively, the IMD comprises an enclosure box, wherein the operational circuitry further comprises a motion sensor, and the enclosure box surrounds the motion sensor and separates the dampening layer from the motion sensor. Additionally or alternatively, the dampening layer is formed in two parts. Additionally or alternatively, the dampening layer comprises a waffled portion defined by ridges and gaps therebetween, the waffled portion having a reduced thermal conductivity than at least one other portion of the dampening layer.

Another illustrative, non-limiting example takes the form of a method of manufacturing an implantable medical device (IMD) comprising: molding a first dampening layer of a dampening material for the IMD; assembling the IMD with the first dampening layer receiving a plurality of components of the IMD; and molding a second dampening layer onto at least portions of the plurality of components while the plurality of components are received by the first dampening layer; wherein the plurality of components includes a battery having a header, and at least one of molding the first dampening layer or molding the second dampening layer comprises forming a void in the region of the battery header to provide thermal isolation thereto.

Additionally or alternatively, at least one of molding the first dampening layer or molding the second dampening layer includes leaving one or more voids in the second dampening layer for use in residual gas analysis of the IMD. Additionally or alternatively, at least one of molding the first dampening layer or molding the second dampening layer includes forming a surface texture on the outside of at least one of the first dampening layer or second dampening layers, the surface texture including one of waffling, bumps or projections, to reduce thermal conductivity in the region of the surface texture.

Another illustrative and non-limiting example takes the form of an implantable medical device comprising a least first and second operational circuitry components each coupled to a printed circuit board assembly (PCBA), a housing, and a dampening layer contained within the housing having first and second dampening layer portions, the second dampening layer portion having a higher thermal conductivity than the first dampening layer portion, wherein: the first operational circuitry component is configured with active and inactive states; the second dampening layer portion surrounds or is adjacent to the first operational circuitry component to dissipate heat generated when the first operational circuitry component is in the active state; and the second dampening layer portion limits heat transfer via the PBCA from the first operational circuitry component to the second operational circuitry component.

This overview is intended to provide an introduction to the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
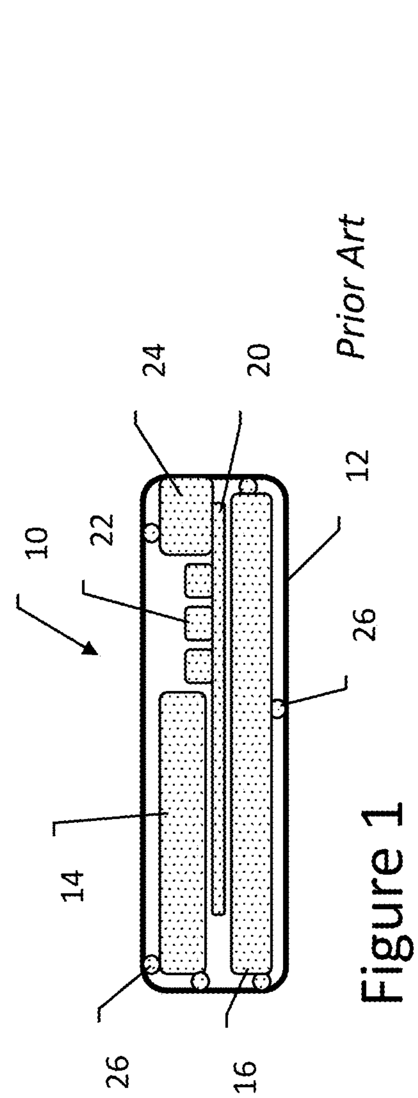
FIGS. 1 and 2 show an example prior art implantable medical device in a simplified section view.
Figure 2:
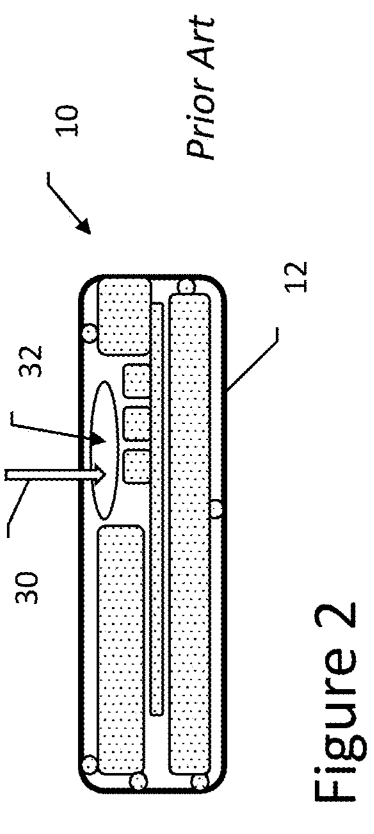

FIGS. 1 and 2 show an example prior art implantable medical device in a simplified section view. Starting with FIG. 1, an implantable medical device 10 is shown in a simplified section view. The device includes a housing 12 which is typically hermetically sealed, and may be made of any suitable material including metal, plastic, or other materials. Titanium is a commonly used material for housing 12.

Inside the housing 12 are various components, shown illustratively as a battery 14, a capacitor 16, and a printed circuit board assembly (PCBA) 20 having a plurality of electric components 22 and coupled to a feedthrough assembly 24, which may be used for coupling the PCBA and components 22 to the outside of the device through a feedthrough, as is well known in the art. While not shown, housing 12 may include a header coupled to the feedthrough assembly 24 having a port or ports for receiving one or more leads.

The drawings herein generally correspond to an implantable defibrillator, which will have one or more relatively large capacitors 16; other implantable medical devices may have componentry of different types and relative sizes. However, the present invention may be used for any implantable medical device, particularly with active implantable medical devices (AIMD). AIMDs may be, for example and without limitation, pacemakers, defibrillators, cardiac monitors, cardiac resynchronization therapy devices, cardiac assist devices neurostimulators, neuromodulators, spinal cord stimulators, Vagus nerve stimulators, deep brain stimulation systems, sacral nerve stimulators, or other systems. Some devices may store a therapeutic substance, such as a drug, if the AIMD is a drug pump, or insulin, if the AIMD is an insulin source. A reservoir for the therapeutic substance may be refillable, if desired. Devices may have a rechargeable battery, if desired.

The components in the device 10 are held in position by a plurality of stabilizing features 26. The stabilizing features may be, for example and without limitation, polymeric dots, bars, rods, or an overall frame that holds the components in a desired position relative to the housing 12 and other components. The rest of the interior of the housing 12 is filled with gas/air. The gas/air provides thermal insulation between the components and the housing, as well as among the components. For example, if a processor is provided as one of the components 22, when that processor is active, convection will not provide much thermal transmission of heat to other components; however, heat may conduct via the PCBA 20 to some extent. The stabilizing features separate components from the housing which, in some examples, may be electrically conductive, such that air serves as a dielectric, though additional shielding may be provided. The stabilizing features also provides a degree of mechanical damping to the housing contents relative to the housing as well as the surrounding environment (whether after implantation or before), which is useful insofar as vibration of the electrical components can lead to various types of failure.

FIG. 2 is similar to FIG. 1, but shows a prior art process step that is performed as part of manufacturing quality management. A residual gas analysis (RGA) step is shown. An RGA probe 30 is inserted into the housing 12, typically by piercing a side of the housing 12, and obtains a sample of the residual gas inside the housing 12 after manufacturing processes are completed. This destructive testing may be performed on a sampled basis, such as a predetermined number of devices per lot, or other manufacturing quantity, to ensure that manufacturing processes are well controlled. The RGA probe 30 will be inserted at a selected location to ensure that the RGA probe 30 obtains a gas sample from a free space 32 inside the housing. That is, in order to perform the RGA test, the RGA probe 30 should not strike the battery or other operational circuitry.

US PG Pat. Pub. 2022/0047876, titled IMPLANTABLE MEDICAL DEVICE WITH RELATIVE MOTION CONTROL, which is incorporated herein by reference, describes an alternative to the use of a frame as shown in FIGS. 1-2 herein. Motion control inside the housing can be controlled by using a dampening layer which is molded onto one or more components. However, doing so also presents new challenges.

Figure 3:
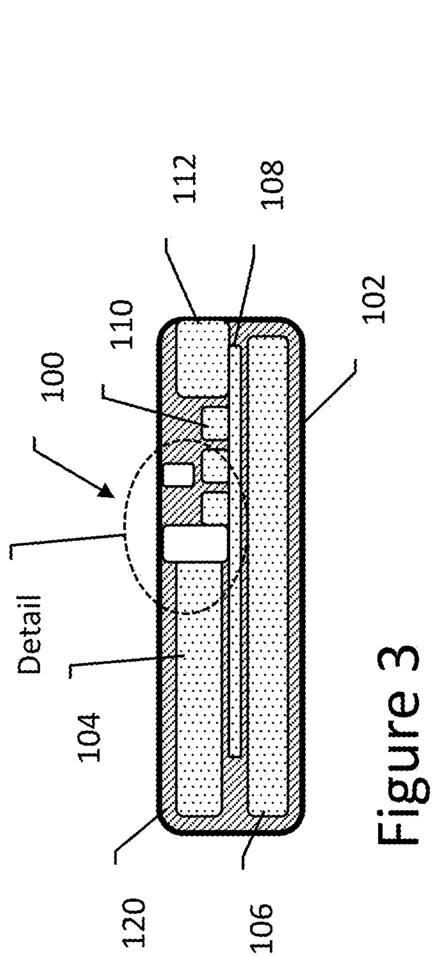
FIG. 3 shows an illustrative example of an implantable medical device with a motion dampening layer, in simplified section view.

FIG. 3 shows an illustrative example of an implantable medical device with a motion dampening layer, in simplified section view. The device 100 includes a housing 102 containing operational circuitry including a battery 104, capacitor 106, and PCBA 108 that carries electronic component 110 and couples to a feedthrough assembly 112. Rather than using the stabilizing features 26 of FIG. 1, the device has a molded dampening layer 120 throughout. The dampening layer may be placed over at least some components, or portions of some components, of the operational circuitry. Additional features are further described with reference to the detail portion shown in FIG. 3, with specific details shown in FIGS. 4A-4C, below.

Figure 4A:
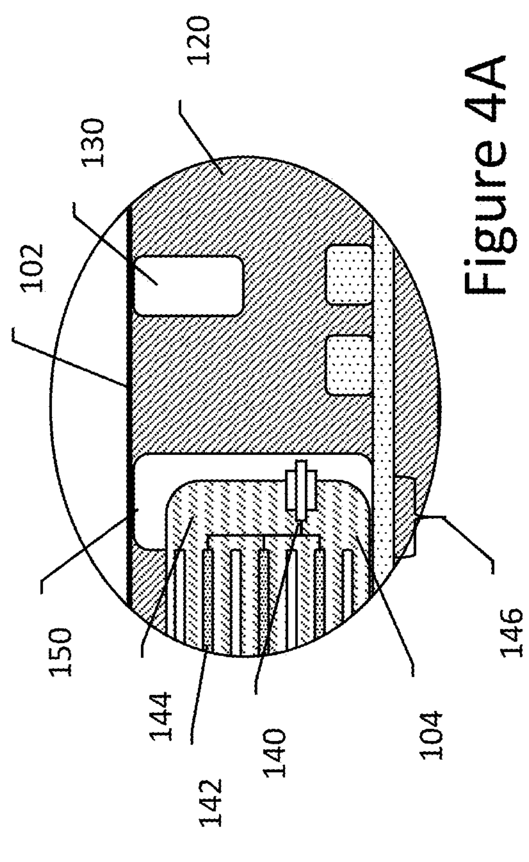
FIGS. 4A-4C are detail views of a portion of FIG. 3.
Figure 4B:
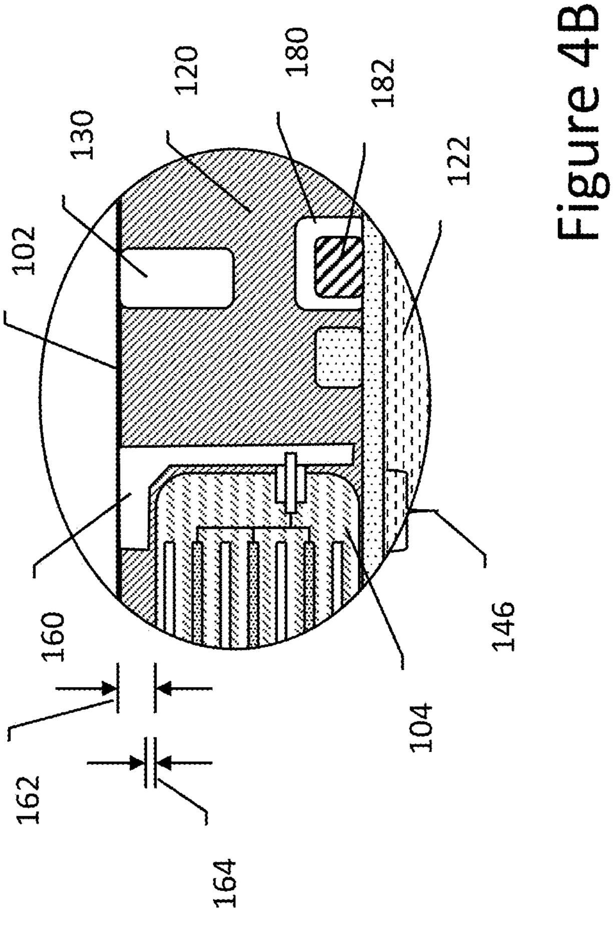
Figure 4C:
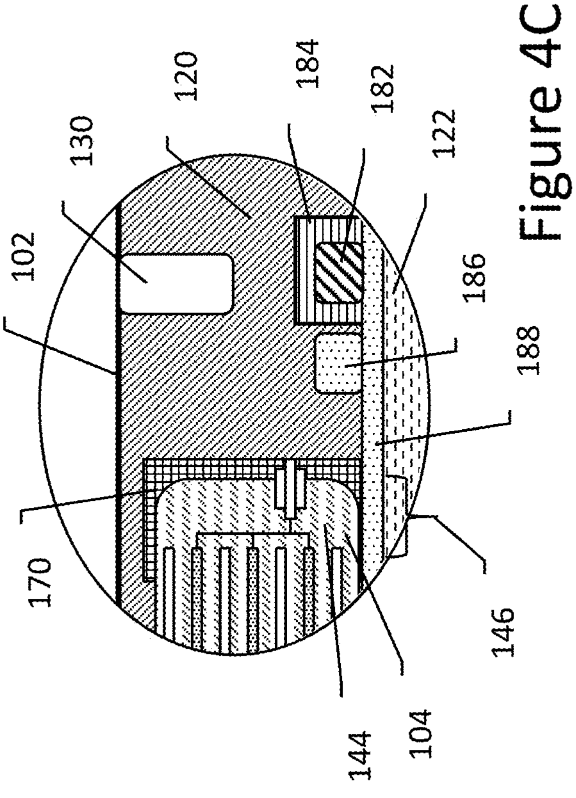

FIGS. 4A-4C are detail views of a portion of FIG. 3. Starting with FIG. 4A, the dampening layer 120 has been modified to provide voids at locations 130 and 150. The void at 130 is provided at a selected location for use in performing the RGA analysis illustrated above in FIG. 2. That is, when an RGA probe is inserted it is desired that the probe not get stuck in the dampening layer.

The void at 150 provides thermal protection to the battery 104. As shown in FIG. 4A, the battery 104 may comprise cathode plates 142 which are separated from anode plates and reside in an electrolyte solution 144. The battery header 146 includes electrical connections from the cathode plates 142 to a feedthrough pin 140, which may be separated from the battery housing at a battery feedthrough using a glass bead, for example and without intending to limit the present invention to any specific battery type or chemistry. Various additional battery components are omitted (separator bags, etc.). The battery header 146 can be understood as roughly extending from the top of the anode/cathode stack to the battery housing itself.

The electrolyte 144 of the battery is typically composed of a solution having at least one salt that can, under certain circumstances, form clusters. For example, with a lithium chemistry battery, such as $LiMnO_2$, lithium clusters can form when high currents are drawn for an extended period of time. Lithium clusters can also form if the battery is subjected to thermal gradients or heat shocks. A thermal gradient can induce a voltage gradient that drives lithium ions to migrate from the colder end of the thermal gradient to the warmer end of the thermal gradient. When such ions come together, electrons can join to form lithium clusters. Lithium clusters generally form where electrolyte contacts anodic surfaces. The lithium clusters, once formed, may accumulate at locations where shorts can be caused between anode and cathode in the battery cell, in particular, near the battery header where connections are made to the cathode and anode feedthroughs 140.

A dampening layer may be a better thermal conductor than the air gaps of the prior art system shown in FIG. 1, allowing heat gradients to arise at unwanted locations, such as near the battery header. Also, when the dampening layer is molded into position, the dampening layer material is at an elevated temperature, for example, 50 C, which significantly higher than human body temperature which is used as the guide for determining appropriate concentrations to use in the electrolyte solution 144 of the battery. Thermally conducted heat gradients during use, or heat shocks during manufacturing, run the risk of causing clusters to form in the electrolyte solution 144. To minimize heat shock and/or heat gradients from being applied to the battery header 146, in an illustrative example, the dampening layer has a void shown at 150, thermally isolating the battery header 146. Such a void 150 may be formed by the use of a protective fixture placed on the battery header 146 during molding, where the fixture is then removed after molding is complete. Other selective molding steps may be used.

FIG. 4B shows another example. Here, the void 160 is formed by, again, selective molding steps such as with the use of a fixture. It is not always easy to create a clean edge on a component without using high pressure/heat during a molding step. Therefore, in the version of FIG. 4B, the dampening layer 120 extends over the battery header 146, but is thinned. For example, the molding process may include use of a fixture that creates voids at 130 and 160. The thickness of the dampening layer 120 over the body of the battery 104 may be as shown at 162, but in the region of the battery header, the dampening layer 120 is thinner, as indicated at 164. Thinning of the dampening layer 120 may reduce thermal shock during the molding process, and, with less dampening material present at the battery header, thermal conductivity of the dampening layer 120 at the battery header is reduced.

FIG. 4B shows another feature. Here, at least one component 182 on the PCBA needs a void 180 to surround it. The component 182 may be, for example, a motion sensor, such as a micro-electro-mechanical system (MEMS) based single or multi-axis accelerometer. In another example, component 182 may be a speaker, used in some implanted systems to issue patient alerts by generating audible tones. The dampening layer 120, if directly molded onto such a sensor or speaker, may reduce its effectiveness. In other examples, the component 182 may be a temperature sensitive component which could be damaged if subjected to heat shock during the molding step. In still further examples, component 182 may be adapted to operate at a relatively higher temperature than human body temperature, meaning it would best operate if thermally isolated from the rest of the system as by providing an air gap around it. A void is therefore provided, as shown at 180.

An additional feature in FIG. 4B is the use of a two-shot dampening layer, including a first part 120, and a second part 122. In the example, the PCBA separates the two parts 120, 122, but this need not be the case. In some examples, a manufacturing method may include dispensing a first part of the dampening layer 122 into a mold or in an AIMD canister with one or more components, or dummy parts in the place of components, in desired positions. In some examples, the complexity of the molding step may be reduced by using a two-part dampening layer.

FIG. 4C shows another alternative. Here, a thermal insulator 170, such as a thermally isolating tape or foam tape, or a preform piece of polymer, foam, etc., is placed over the battery header 146 prior to molding the dampening layer 120 into place. Doing so may simplify the molding fixture and process. Now a void is formed in the dampening layer, where the void is filed by the thermal insulator 170. The device here again contains component 182 that is to be kept out of the dampening layer 120. Component 182 is provided an isolation box 184, which may define an air gap or space thereabout. The isolation box 184 may instead be a piece of foam, if desired; using an isolation box rather than a mold fixture, such as a removable mandrel, may simplify the processing steps. It should be understood from FIG. 4C that a void in the dampening layer 120 may be filled by a different material or component, as desired; the void need not be empty or only filled with gas to be a void, at least relative to the dampening layer 120. FIG. 4C also shows the use of a two-part dampening layer 120, 122.

While the above explains isolation box 184 is provided around component 182, in an alternative example, the region shown at 184 may be filled with a highly thermally conductive material, such as a thermally conductive epoxy or polymer, for example. A purpose may be to improve or direct heat dissipation of a component 182 away from the PCBA on which it is mounted, reducing the likelihood of heat energy conducting to nearby components on the PCBA. In an example, an implantable medical device having a rechargeable battery may have associated therewith an inductive coil or RF coil for wirelessly receiving power for battery charging purposes. Such a recharging coil can generate heat during recharging, for example, if there is misalignment with a primary coil on an external charger, or if temporary conditions cause a current spike. The use of more highly thermally conductive material in a portion of the molded dampening layer 120 may help to spread the heat that is generated away from the coil or other component prone to heating.

In another example, the component 182 may be a relatively higher power device used at a low duty cycle. For example, it is known to include a microcontroller or microprocessor in an implantable medical device to perform various high level functions of the device. To prevent early battery depletion, the microcontroller or microprocessor may be configured for a relatively low duty cycle operation, such as operating only when called via an interrupt, or according to a clocked wakeup cycle, to achieve a duty cycle of less than 10%, or less than 1%. In another example, a telemetry antenna and associated driver are configured to perform periodic telemetry wakeups to listen to telemetry interrogations at a low duty cycle, of less than 10% or less than 1%. In another example, a charging circuit for a high power stimulation system, such as a defibrillator, includes one or more component used to generate very high currents on a very limited basis; for example, a transformer used as a DC:DC step up in an implantable defibrillator may be operated for up to 20 seconds in a single charging cycle, with charging taking place only a few times each year. For each of these systems, during the short time of actual use, a relatively larger amount of current is used as compared to the average current/power used in the device on an ongoing basis. The heat generated by such a component may be accommodated in some examples by providing relatively higher thermal conductivity portion at 184 to spread heat from component 182 to prevent such heat being sunk via the PCBA to impact other parts of the electrical circuitry. Further, rather than a symmetric shape as shown at 184, the volume of higher thermal conductivity may be shaped to direct heat energy away from any sensitive components or regions of sensitive components, so as to direct heat energy away from the header of the battery.

In an example, the system has first and second components 182, 186 on the PCBA 188, and the first component 182 has active and inactive states, generating heat when in the active state. The dampening layer may be understood as having a first portion shown at 120 and a second portion shown at 184, where the second portion 184 has a higher thermal conductivity than the first portion 120, allowing heat generated while the first component 182 is in an active state to dissipate via the second portion 184, rather than passing via the PCBA to the second component 186, and/or being absorbed into the PCBA in an amount that damages any traces or components thereof directly, and/or being absorbed into the PCBA to create localized stress due to heating-induced expansion/contraction or stiffening/relaxing of the PCBA. Moreover, the second portion 184 having a relatively higher thermal conductivity than the first portion 120 of the dampening layer also reduces heat transfer to the battery. For example, the second portion 184 may have a thermal conductivity that is at least 25%, or 50%, or 75%, or 100% higher than the thermal conductivity of the first portion 120.

Region 170 in this example may be understood as still a third portion of the dampening layer, and may have either a higher or lower thermal conductivity. A higher thermal conductivity may be useful so that a heat gradient in the first portion 120 does not translate to the battery header—that is, even if a heat gradient is observed on the first portion 120, region 170 provides ready heat transfer across the battery header region wiping out the heat gradient. A lower thermal conductivity may be used instead, to prevent or limit heat transfer from first portion 120 to the region 170 entirely.

Figure 5:
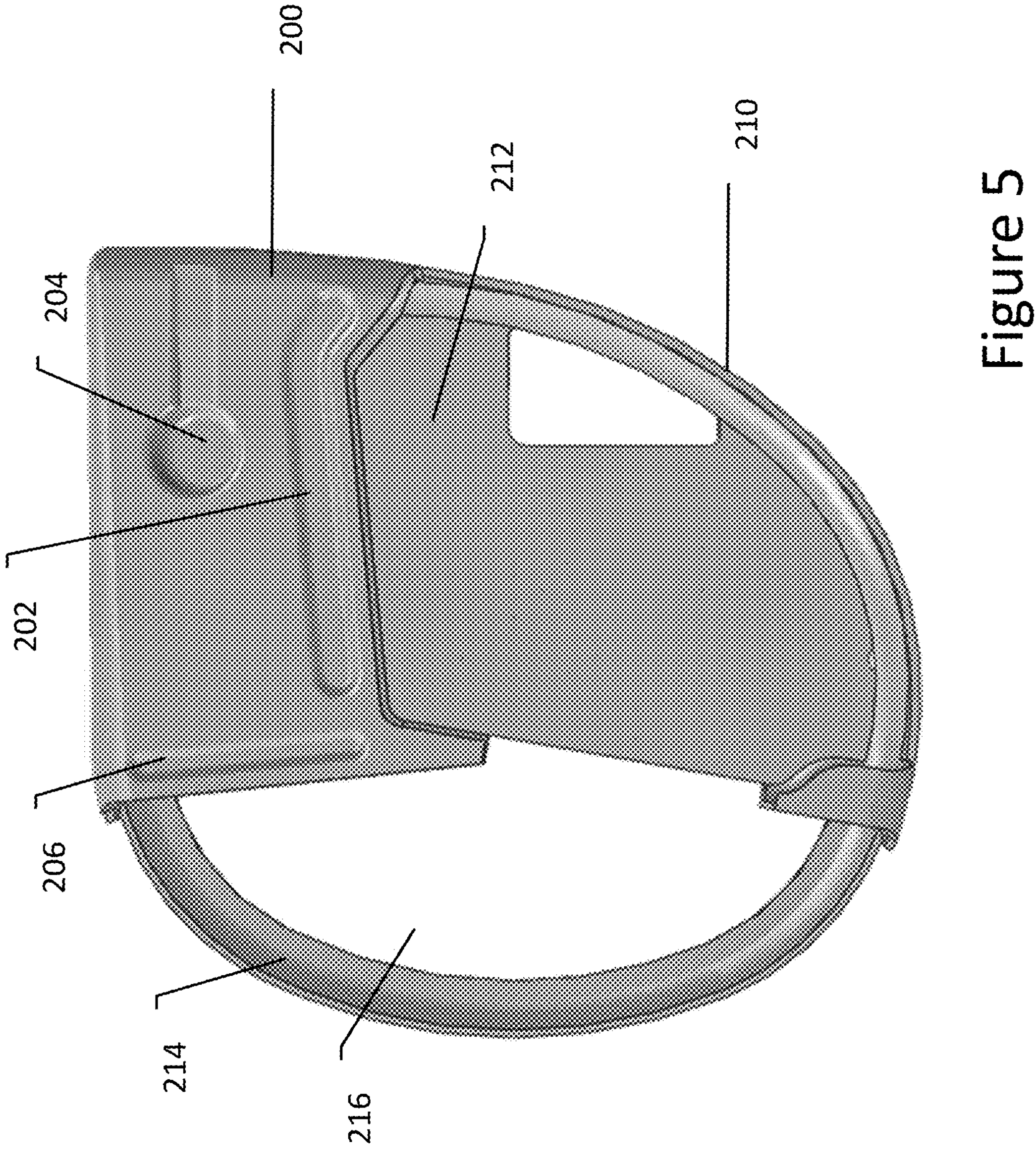
FIGS. 5-7 are various views of an illustrative dampening layer.

FIG. 5 is a perspective view of an illustrative dampening layer. The dampening layer 200 can be seen to include a channel defining a void at 202, which is positioned in this example to correspond to the header of a battery, as well as a divot forming void 204 for use in RGA. The dampening layer 200 may be formed in a single shot molding process, or there may be multiple steps to form multiple parts of the dampening layer.

The dampening layer 200 may be a moldable material such as, but not limited to, a thermoplastic, elastomer, thermoplastic elastomer (TPE), or hot melt polymer. In some examples, the dampening layer 200 may be a composite or blend including two or more polymeric materials. One example of material that may be suitable is a thermoplastic elastomer, styrene-ethylene-butylene-styrene (SEBS). Other examples include high performance polyamide (PA) hotmelt adhesives, such as Henkel® Macromelt® 653 and Henkel® Macromelt® 673. These are moldable under low pressure (between 2 and 40 bar), are solvent free, have short cycle time (10-50 seconds), do not require a heat curing process, and adhere to polar plastics such as polyamide, acrylonitrile butadiene styrene (ABS), and polyvinyl chloride (PVC). In some examples, polyamide hotmelt molding can achieve enhanced sealing and improved protection of electrical components as compared to conventional 2-part casting materials (epoxy) or potting resins or silicones. The polyamide hotmelt molding material is a single component material that provides water-tight encapsulation and electrical insulation. Other hotmelts may be used, such as the copolymers Henkel® Technomelt® AS4226, or Henkel® Technomelt® AS8998 (a polyolefin). Further examples include maskants such as Dymax® Speedmask® 726-SC and Dymax® Speedmask® 728-G. These moldable acrylated urethanes have a fast cure time (8-10 seconds) under UV or visible light, and have a Shore D hardness of 40-55. Another example of a suitable moldable material is Robnor ResinLab® EL227CL, a two-part low viscosity polyurethane resin with a Shore A hardness of 16. Other acrylated urethanes may be used, such as Dymax® Speedmask® 9-7001 or Dymax® Speedmask® 9-20479-B-REV-A. A further example of a moldable material is polycaprolactone.

The dampening layer 200 in FIG. 5 also includes a channel at 206, generally along the region of the header of the capacitor stack, which would be positioned to correspond to a void area 216. The dampening layer 200 may also include an outer rim 210 and 214 positioned to provide mechanical stabilization against the outer canister of the AIMD, with a first part 210 surrounding the battery in this example, and a second part 214 surrounding the capacitor. A void is generally provided at 212 and surrounds a portion of the battery away from the battery header.

Figure 6:
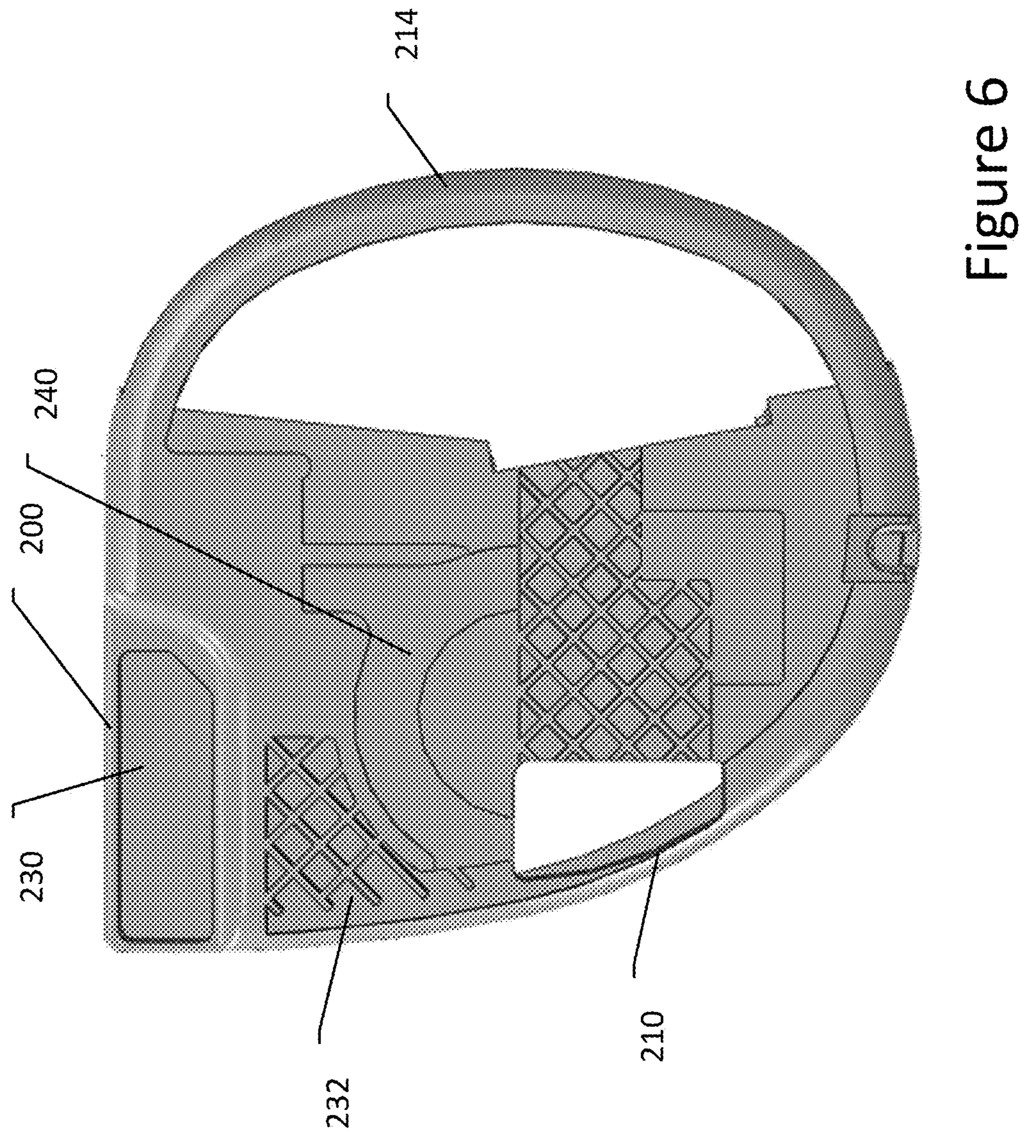

FIG. 6 shows the dampening layer 200 again, with the opposite face shown. Here, the dampening layer 200 again includes the outer rim 210, 214. The surface shown in FIG. 6 would be positioned against the AIMD canister. Waffling is provided at 232 as an outer texture on the dampening layer 200, forming a waffled portion defined by cross-hatched ridges and gaps. Other designs may be used, including circular ridges, or discontinuous bumps, pillars, ridges, teeth, etc. The waffled portion may serve several purposes including reduced thermal conductivity where the waffling 232 is present, as well as reducing the total quantity (and thus total mass) of the dampening layer 200. The dampening layer may include additional gaps/features/surface contours, such as that shown at 240 as corresponding to a piezo-speaker for the device. For example, at 240 an indentation is formed for receiving a portion of the piezo-speaker without encapsulating it. A void is provided at 230 corresponding to the AIMD feedthrough structure.

Figure 7:
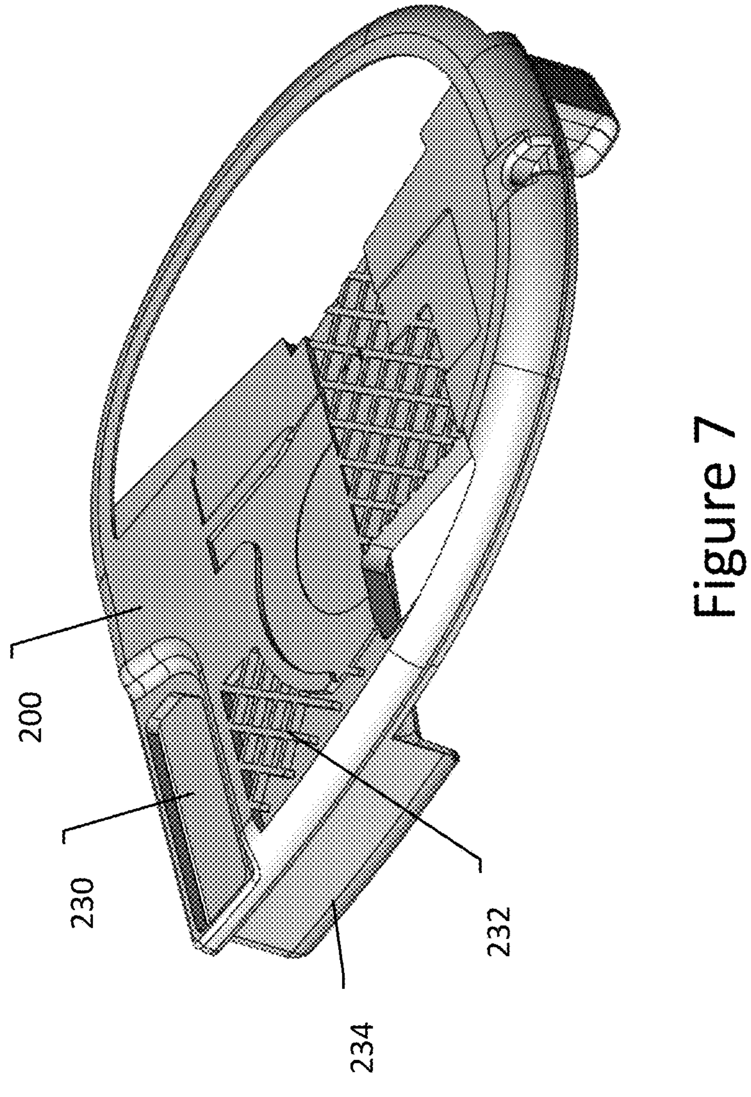

FIG. 7 shows another angle. Here, the dampening layer 200 again shows the waffling at 232. Other surface texture, such as an arrangement of bumps, small pillars or other projections may be used instead to provide air gaps in such regions. As can also be seen in this angle, walls are defined as shown at 234 around select portions of the circuitry; in this example the wall 234 surrounds the processor and other operational circuitry, creating a degree of separation relative to outer canister of the AIMD and also providing physical separation, including dielectric insulation, between different parts of the AIMD such as the batteries, capacitors and/or processor, logic, memory and other active circuitry.

In some examples a two-part dampening layer 200 is provided, as noted above. In some such examples, a first part is provided with receiving cavities or other structures into which device components are placed. The first part may be placed or formed inside of the canister of the AIMD, and components of the AIMD may be either placed in the receiving cavities after formation, or may be positioned so that the first part is formed around the components of the AIMD. The second part of the dampening layer 200 is then placed in a second molding step. During the second molding step, the second part of the dampening layer 200 may become secured to the first part through contact made during the molding step between the two parts. Alternatively, the two parts may not be contacted to one another, as desired. After the second molding step, the canister of the AIMD is then closed by, for example, welding two parts of the canister together along a weld seam.

In some examples, the design may include an air pocket between the capacitor(s) (particularly with an implantable defibrillator having capacitors sized greater than 10 microfarads, sometimes in the range of more than 50 microfarads) and the one or more battery cells provided in a given system. In some examples, a dampening layer, such as a two part dampening layer shown above, may be used along with one or more spacers. For example, the dampening layer design may provide open spaces or gaps alongside relatively larger structures such as the battery cells or capacitor(s), and separate spacers and/or dielectric tape pieces may be selectively placed to maintain a gap relative to, for example, the outer canister and/or a dump or electromagnetic interference shield, providing both dielectric and thermal isolation as desired. Since air or injected gas in the canister may be a better thermal isolator than the dampening layer and/or any such tape or spacers, the positioning of materials may also help steering thermal flux as desired.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. An implantable medical device (IMD) comprising a housing and, inside the housing:

operational circuitry for performing one or more IMD functions;

a battery coupled to the operational circuitry to provide power for the one or more IMD functions, the battery including a header region containing electrical connections to a battery feedthrough pin, the battery feedthrough pin used for electrical connection from inside the battery to the operational circuitry;

a dampening layer molded over portions of the operational circuitry and at least a first portion of the battery, wherein the dampening layer comprises a first void positioned over the header region of the battery to provide thermal isolation to the header region of the battery.

2. The IMD of claim 1, wherein the dampening layer has a first thickness over the first portion of the battery, and a second thickness over the header region of the battery, wherein the second thickness is less than the first thickness due to the void.

3. The IMD of claim 1, wherein the dampening layer is omitted entirely over at least a part of the header region of the battery.

4. The IMD of claim 1 wherein the first void of the dampening layer is filled with a thermally isolating tape applied over the header region of the battery.

5. The IMD of claim 1 wherein the first void of the dampening layer is filled with a preform device that is applied over the header region of the battery.

6. The IMD of claim 1, wherein the dampening layer comprises a second void positioned for use in a residual gas analysis test.

7. The IMD of claim 1, wherein the operational circuitry further comprises a speaker, and the dampening layer comprises a third void positioned over the speaker, or the dampening layer comprises an indentation for receiving the speaker without encapsulating the speaker.

8. The IMD of claim 1, further comprising an enclosure box in the housing, wherein the operational circuitry further comprises a motion sensor, and the enclosure box surrounds the motion sensor and separates the dampening layer from the motion sensor.

9. The IMD of claim 1, wherein the dampening layer is formed in two parts.

10. The IMD of claim 1, wherein the dampening layer comprises a waffled portion defined by ridges and gaps therebetween, the waffled portion having a reduced thermal conductivity than at least one other portion of the dampening layer.

11. An implantable medical device (IMD) comprising a housing and, inside the housing, each of:
- operational circuitry for performing one or more IMD functions;
- a battery coupled to the operational circuitry to provide power for the one or more IMD functions, the battery including a header region containing electrical connections to a battery feedthrough pin, the battery feedthrough pin used for electrical connection from inside the battery to the operational circuitry;
- a dampening layer molded over portions of the operational circuitry and at least a first portion of the battery, wherein the dampening layer comprises a first void positioned for use in a residual gas analysis test.

12. The IMD of claim 11, further comprising a molded thermal isolation layer on the header region of the battery, thermally separating the dampening layer from the header region of the battery.

13. The IMD of claim 11, wherein the dampening layer has a first thickness over the first portion of the battery, and a second thickness in a selected area over at least part of the headspace region of the battery, the selected area of the dampening layer having an air gap thereover, wherein the second thickness is less than the first thickness.

14. The IMD of claim 11, wherein the dampening layer has a second void defining an air gap over the header region of the battery.

15. The IMD of claim 11, further comprising an enclosure box in the housing, wherein the operational circuitry further comprises a motion sensor, and the enclosure box surrounds the motion sensor and separates the dampening layer from the motion sensor.

16. The IMD of claim 11, wherein the dampening layer is formed in two parts.

17. The IMD of claim 11, wherein the dampening layer comprises a waffled portion defined by ridges and gaps therebetween, the waffled portion having a reduced thermal conductivity than at least one other portion of the dampening layer.

18. An implantable medical device (IMD) comprising:
- an operational circuitry including at least first and second components;
- a printed circuit board assembly (PCBA) to which each of the at least first and second components are secured;
- a housing; and
- a dampening layer contained within the housing having first and second dampening layer portions, the second dampening layer portion having a higher thermal conductivity than the first dampening layer portion, wherein:
  - the second dampening layer portion surrounds or is adjacent to the first component to spread and/or dissipate heat generated by the first component; and
  - the second dampening layer portion limits heat transfer via the PBCA from the first component to the second component.

19. The IMD of claim 18, wherein the first component is configured with active and inactive states, and a duty cycle of less than 10% for the active state.

20. The IMD of claim 19, wherein the duty cycle is less than 1%.

* * * * *